United States Patent [19]
McCue et al.

[11] Patent Number: 5,676,668
[45] Date of Patent: Oct. 14, 1997

[54] FEMORAL LOCATING DEVICE ASSEMBLY

[75] Inventors: Diana McCue, Pocasset; Richard Techiera, Avon; Gary P. Trottier, Whitinsville, all of Mass.; Donald Marcoccio, Cumberland; David L. LaSalle, Woonsocket, both of R.I.

[73] Assignee: Johnson & Johnson Professional, Inc., Raynham, Mass.

[21] Appl. No.: 602,536

[22] Filed: Feb. 20, 1996

[51] Int. Cl.⁶ ................................................. A61B 17/56
[52] U.S. Cl. .............................. 606/87; 606/88; 606/102
[58] Field of Search ............................. 606/88, 87, 89, 606/95, 86, 102, 96

[56] References Cited

U.S. PATENT DOCUMENTS

| | | | |
|---|---|---|---|
| 4,474,177 | 10/1984 | Whiteside | 606/88 |
| 4,703,751 | 11/1987 | Pohl | 128/92 |
| 4,736,737 | 4/1988 | Fargie et al. | 606/88 |
| 5,342,368 | 8/1994 | Petersen | 606/88 |
| 5,423,827 | 6/1995 | Mumme et al. | 606/96 |
| 5,445,642 | 8/1995 | McNulty et al. | 606/88 |
| 5,454,816 | 10/1995 | Ashby | 606/88 |
| 5,484,446 | 1/1996 | Burke et al. | 606/96 |
| 5,486,178 | 1/1996 | Hodge | 606/88 |

*Primary Examiner*—Michael Buiz
*Assistant Examiner*—Julian W. Woo
*Attorney, Agent, or Firm*—Susan M. Schmitt

[57] ABSTRACT

An improved femoral locating device and system is provided including an angularly adjustable locking alignment portion for appropriately aligning the posterior end of the locator. Another feature of the system provides a cutting block moveable from distal to proximal or proximal to distal to alter the thickness of the cut and holding it securely once the thickness of the cut is determined. Finally, another feature of the system includes the ability to raise and lower the cutting block without changing the valgus angle.

10 Claims, 7 Drawing Sheets

FEMORAL LOCATING DEVICE ASSEMBLY

FIELD OF THE INVENTION

The present invention relates to a femoral locating device used in knee replacement procedures, for aligning and locating the distal femoral cutting block with respect to the medullary canal and distal condyles.

BACKGROUND OF THE INVENTION

In a knee replacement surgical procedure the distal condyles of the femoral bone are prepared by making an initial cut in a portion of the distal condyles, separately making anterior, posterior and two chamfer cuts, and placing a femoral implant on the distal end of the femur. In performing this procedure the femoral component should be aligned perpendicular to the mechanical axis of the leg. The mechanical axis is defined as a straight line draw through three landmarks: center of the hip, center of the knee, and center of the ankle. In contrast, the anatomical axis is identified by the line of an intramedullary rod inserted into the medullary canal.

A distal femoral cut is made in appropriate valgus by determining the angle between the anatomical and mechanical axes of the femoral shaft. The difference between the intramedullary rod axis and the mechanical axis is defined as the valgus angle.

In order to make an initial distal cut perpendicular to the mechanical axis, a femoral locating device is inserted over the intramedullary rod and rests contacting the distal condyles of the femur. The angle of the femoral locator is adjusted to be perpendicular to the mechanical axis as opposed to the anatomical axis defined by the intramedullary rod. An external alignment tower is attached to the locating device. The tower includes holes for accepting external alignment rods which are used to confirm the mechanical axis of the patient's leg. The orientation of the locator is adjusted so that the femoral locating device establishes a cutting plane perpendicular to the mechanical axis of the femur. This adjustment to the mechanical axis orientation has been made using various means in the prior art.

In one embodiment the body of the locator is coupled to one of a plurality of bushings having various predetermined valgus angles. Once an appropriate bushing is selected, a distal femoral cutting block is coupled to the locator by way of an outrigger set a predetermined distance above the center line of the intramedullary rod. The distal femoral cutting block measures and guides the cut made in the femoral bone. The distal femoral cutting block is held in position by two ball plungers which correlate to 'V' shaped notches in the femoral locating device outrigger. The cutting block is attached to the anterior cortex of the femur with two Steinmann pins introduced through holes in the cutting block. Additional holes are arranged so that the cut may be adjusted distally or proximally in an even amount, typically in increments of 2 degree. The cutting block is moved off the pins and reset onto the pins through the additional holes, thereby changing the distal cut location with respect to the condyles. The cut is made across the distal end of the femur. This distal cut is used as a reference to locate instruments and complete the other femoral outs prior to placing the femoral implant in position.

The disadvantages of this method include the requirement to remove the intramedullary rod in order to place various bushings on the rod in an attempt to match the valgus angle. Every time the bushing is changed, the rod must be removed entirely from the bone. Furthermore, the number of bushings required are numerous, and the angles are limited to increments in degrees between bushings, which are typically about 2 degree increments. Also, the distance of the distal femoral cutting block is fixed over the intramedullary rod so that on most patients, there is a gap between the bottom of the block and the anterior cortex. This gap complicates the drilling procedure and makes accurate cutting more difficult. Furthermore, the ball plungers holding the block are subject to wear and can be easily displaced. The block may shift position while the surgeon attempts to drill to place the steinman pins.

Accordingly, one object of the present invention is to provide an improved angle adjustment means for orienting the femoral locating device in alignment with the mechanical axis and preferably capable of locking the angle into its selected position.

Another object of the present invention is to provide a means for moving the cutting block distally and proximally on the femoral locating device outrigger to set the amount of distal resection of the femur. The location should be held firmly to avoid the block shifting during Steinman pin drilling.

Another object of the present invention is to provide a means for raising and lowering the cutting block so that the cutting block may be in close proximity to the bone when drilling to place the Steinman pins which fixate the block to the anterior cortex.

SUMMARY OF THE INVENTION

The present invention provides a femoral locating assembly including an angularly adjustable alignment portion for appropriately aligning the proximal end of the femoral locating device. The alignment portion is arranged to be securely locked into position when the appropriate valgus angle is selected.

Another feature of the invention provides a means for moving the cutting block distal to proximal or proximal to distal to alter the thickness of the cut and holding it securely once the thickness of the cut is determined.

Another feature of the invention includes a means for raising and lowering the cutting block without changing the valgus angle. This feature allows the cutting block to be aligned in closer proximity to the condyle portion of the femur so that cutting is more reliably achieved.

DETAILED DESCRIPTION OF THE INVENTION

Figure 10:
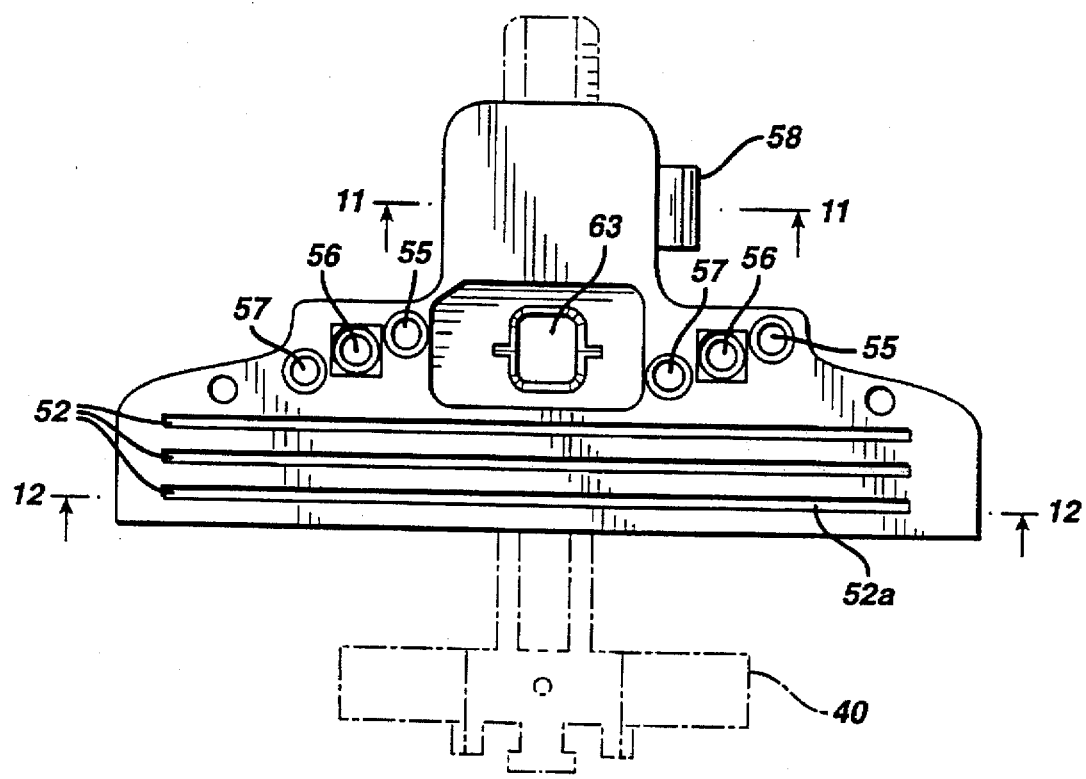
FIG. 10 illustrates a top anterior view of the distal femoral cutting block.
Figure 11:
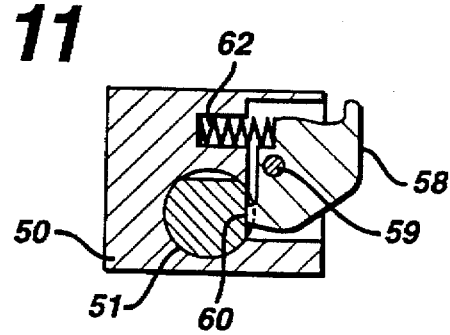
FIG. 11 illustrates a cross sectional view of the button portion of the distal femoral cutting block of FIG. 10 along the lines 11—11.
Figure 12:
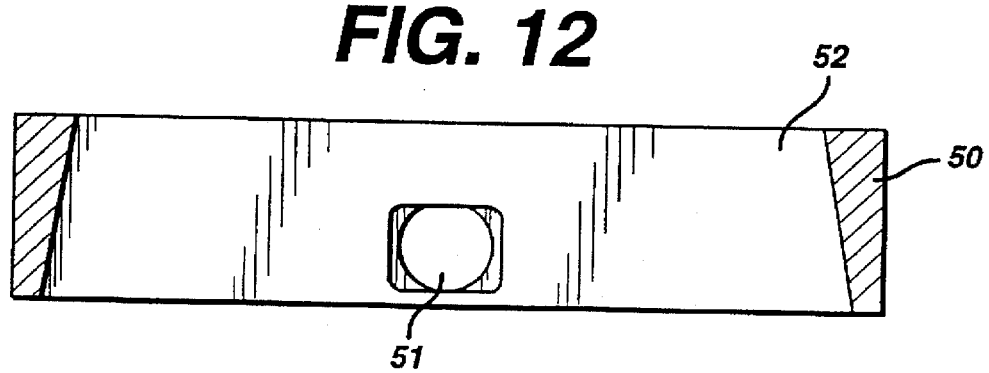
FIG. 12 illustrates a cross sectional distal view of the cutting block of FIG. 10 along the lines 12—12.

FIGS. 1–12 illustrate a femoral locating and alignment system for preparing and performing an initial femoral distal cut. The system (FIG. 9) comprises a femoral locating device 10 (FIGS. 1–6), an outrigger 40 (FIG. 7), an alignment tower 70 (FIGS. 8, 9) and a cutting block 50 (FIGS. 10–12).

Referring now to FIGS. 1–6 there is illustrated a femoral locating device or locator 10 comprising a body 12, a pivoting member 14 pivotally coupled to the body 12, and a condyle interfacing end 16 located on the proximal side of the body 12.

The pivoting member 14 extends into an opening 17 within the interfacing end 16 and is movably coupled to the body 12 by way of pivoting pins 15. The pivoting member 14 includes an opening 32 extending distal to proximal through the pivoting member 14. The opening 32 receives an intermedullary rod (not shown) which extends through the opening 32 into the intermedullary canal of the femur to establish an anatomical axis.

The pivoting member 14 has teeth 18 on the bottom portion of its distal end. The teeth 18 secure the pivoting member 14 to the body 12 by engaging with teeth 19 of a button 20 on the body 12 to prevent pivotal movement of the member 14 with respect to the body 12 or vica versa.

Button 20 is biased in a teeth engaging direction by way of spring 21. Button 20 includes a finger pad 22 which when depressed, disengages teeth 19 from teeth 18 to permit pivotal movement of pivoting member 14 with respect to body 12 or vica versa.

Femoral locator 10 further includes a locking member 24 located at the distal end of the body 12, comprising deflectable arms 25 with locking tabs 26a and locking tabs 26b. The arms 25 extend into a slot 29 on the distal side of the body 12. The arms 25 fit around pin 27 in body 12. The arms 25 are locked into position by tabs 26 which impede movement of the locking member 24 by engaging with pin 27. The distance between tabs 26b is smaller than the diameter of the pin 27 so that the tabs 26b will not move past pin 27 without an arm deflecting force applied to the locking member 24.

Figure 1:
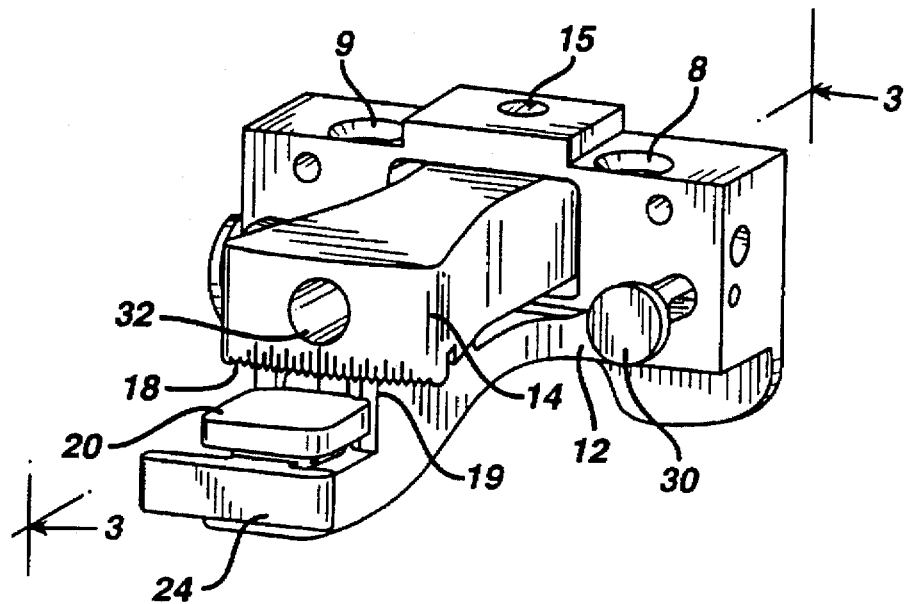
FIG. 1 illustrates a distal perspective view of the femoral locating device of the present invention.
Figure 2:
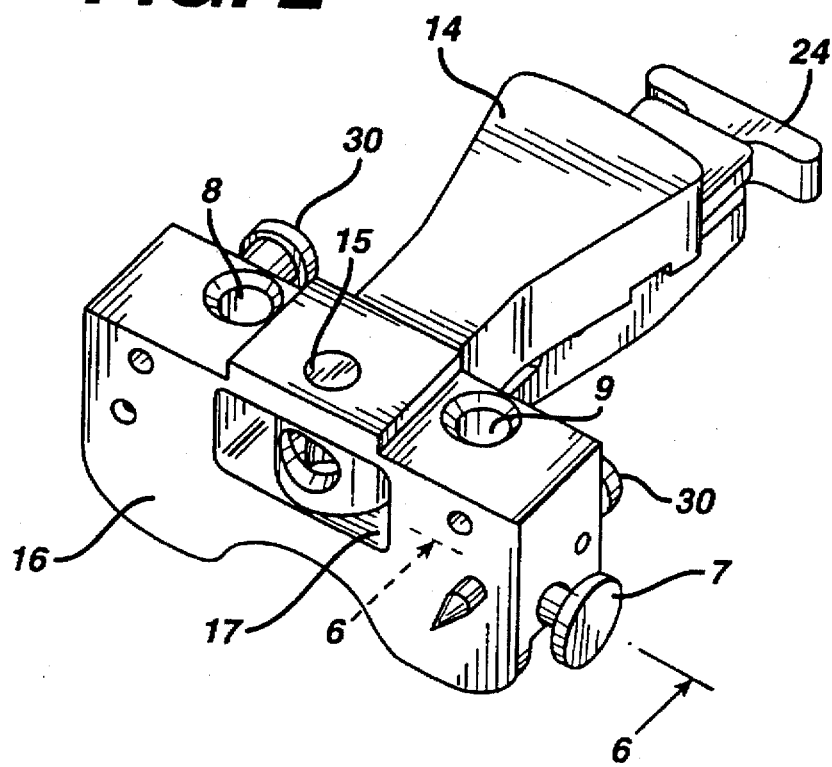
FIG. 2 illustrates a top anterior view of the femoral locating device of the present invention.
Figure 3A:
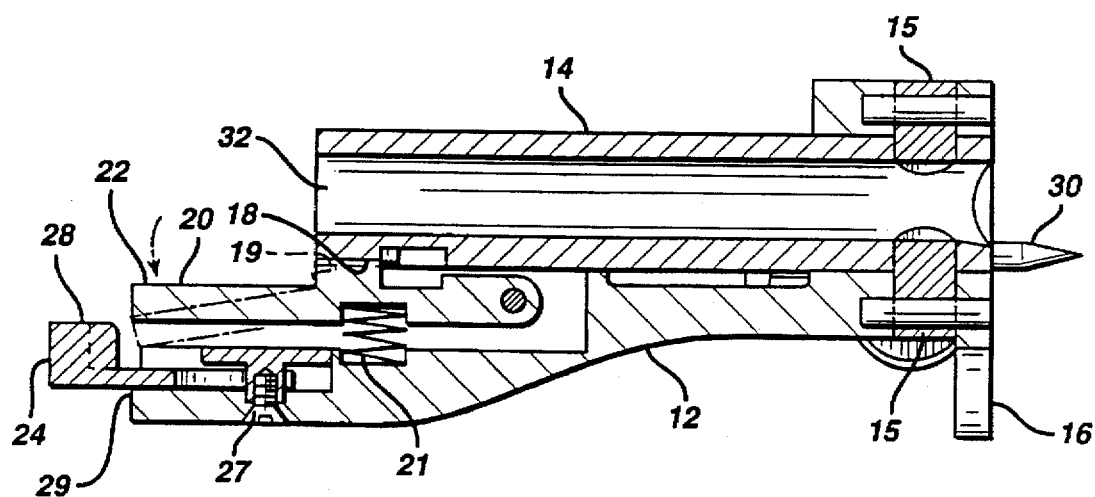
FIG. 3A illustrates a side cross sectional view of the femoral locating device of FIG. 1 along the lines 33 in an unlocked position.
Figure 3B:
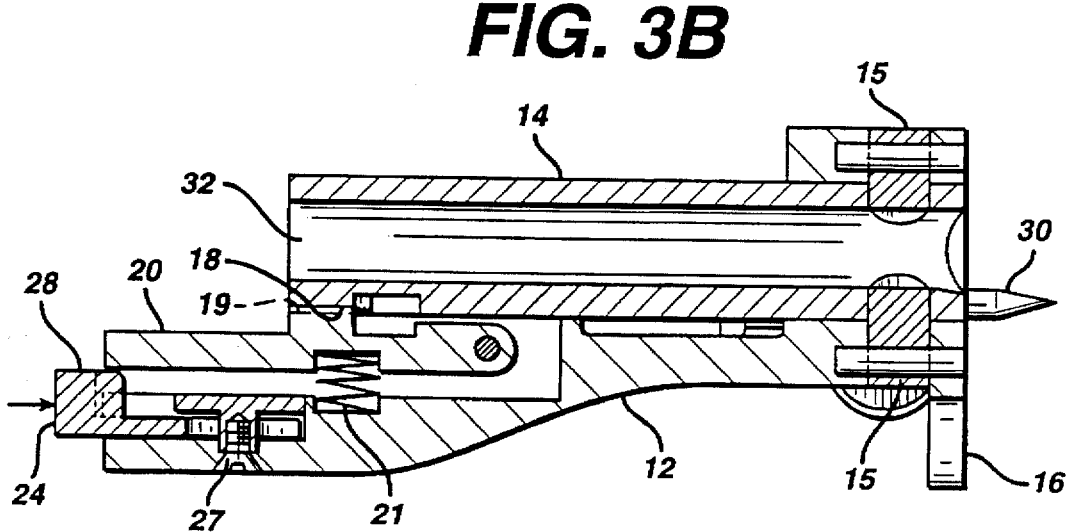
FIG. 3B illustrates a side cross sectional view of the femoral locator in FIG. 1 in a locked position.
Figure 4A:
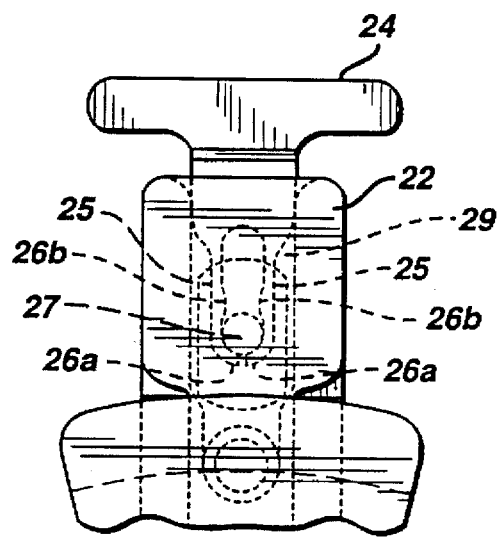
FIG. 4A illustrates a top plan view of the locking mechanism at the distal side of the femoral locating device in an unlocked position.
Figure 4B:
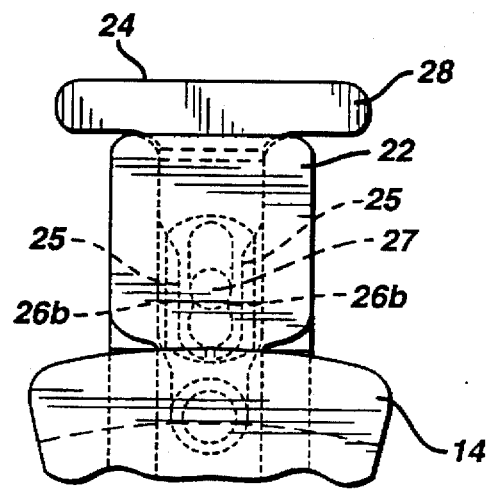
FIG. 4B illustrates a top plan view of the locking mechanism at the distal side of the femoral locating device in a locked position.
Figure 5:
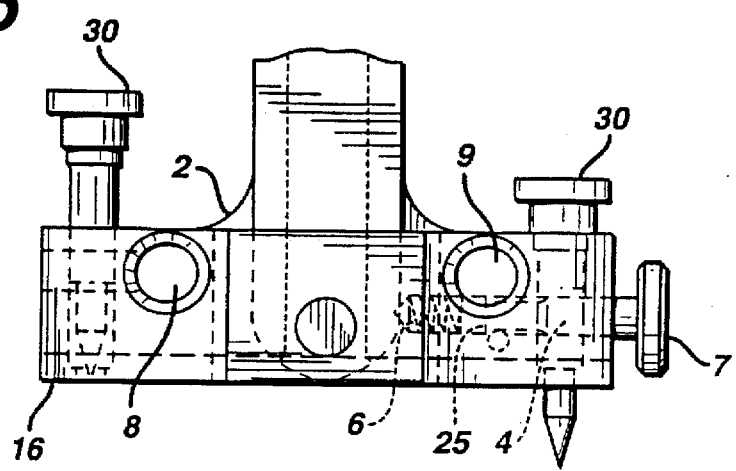
FIG. 5 illustrates a top plan view of the proximal portion of the locking mechanism for locking the outrigger to femoral locating device.
Figure 6:
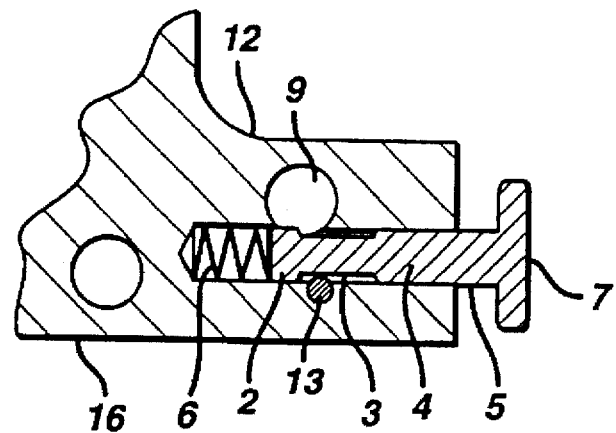
FIG. 6 illustrates a cross sectional view of the proximal portion of the locking mechanism of FIG. 2 along the lines 6—6, illustrating the mechanism for raising and lowering the outrigger.

The locking member 24 has two positions: a first unlocked position in which a locking ledge 28 is retracted in a direction from the body 12 (FIGS. 3A and 4A) and a second locked position in which the locking ledge 28 extends in a direction towards the body 12 (FIGS. 3B and 4B). The tabs 26b provide resistance to locking member movement from the unlocked to the locked position and vica versa. In the unlocked position, the locking member 24 is free from contact with the button 20. In the locked position, a ledge 28 on the locking member 24 extends under the button 20 to present depression of the button 20 thereby preventing the teeth 19 of the button 20 from disengaging from the teeth 18 of the pivoting member 14.

The teeth 18 and 19 are arranged in radial increments about the pivoting pins 15 preferably of about 1°. When the locking member 24 is in the locked position, the pivoting member 14 is thereby locked into an angular position with respect to the body 12.

Figure 7:
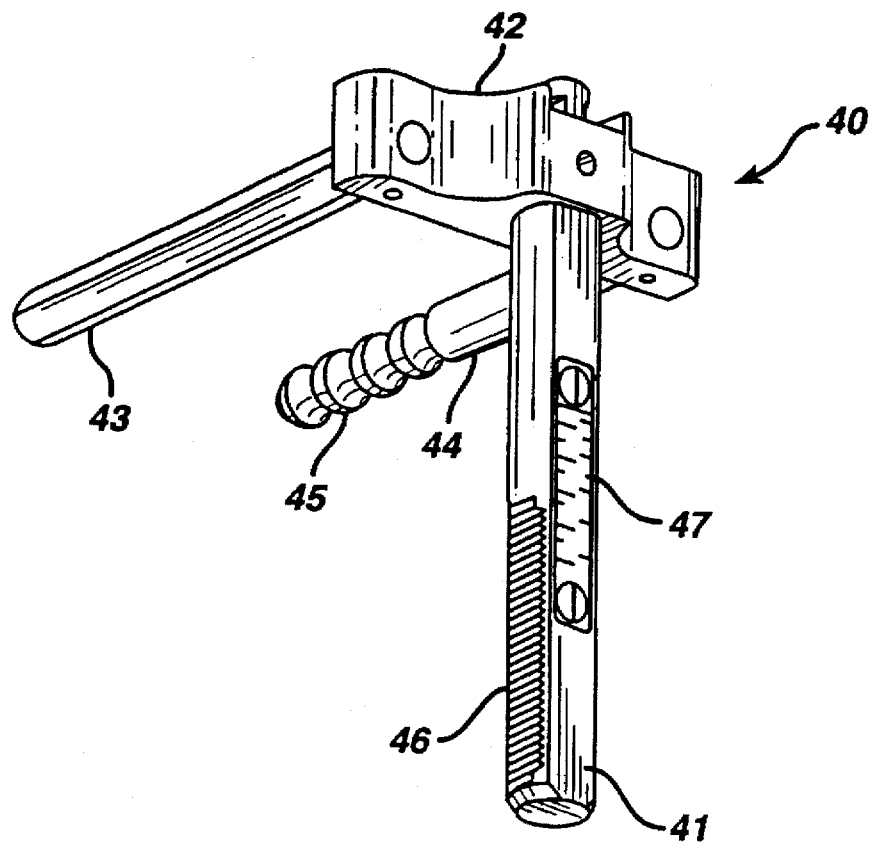
FIG. 7 illustrates a perspective view of the Femoral Locating Device Outrigger of the present invention.

The system of the preferred embodiment of the present invention further comprises an outrigger 40 illustrated in FIG. 7 comprises a D-shaped shaft 41 coupled to the outrigger body 42 with a diamond pin shaped leg 43 and a locking leg 44 having grooves 45 for locking the outrigger 40 to the body 12 in a position parallel relative to the intramedullary rod axis.

Figure 8:
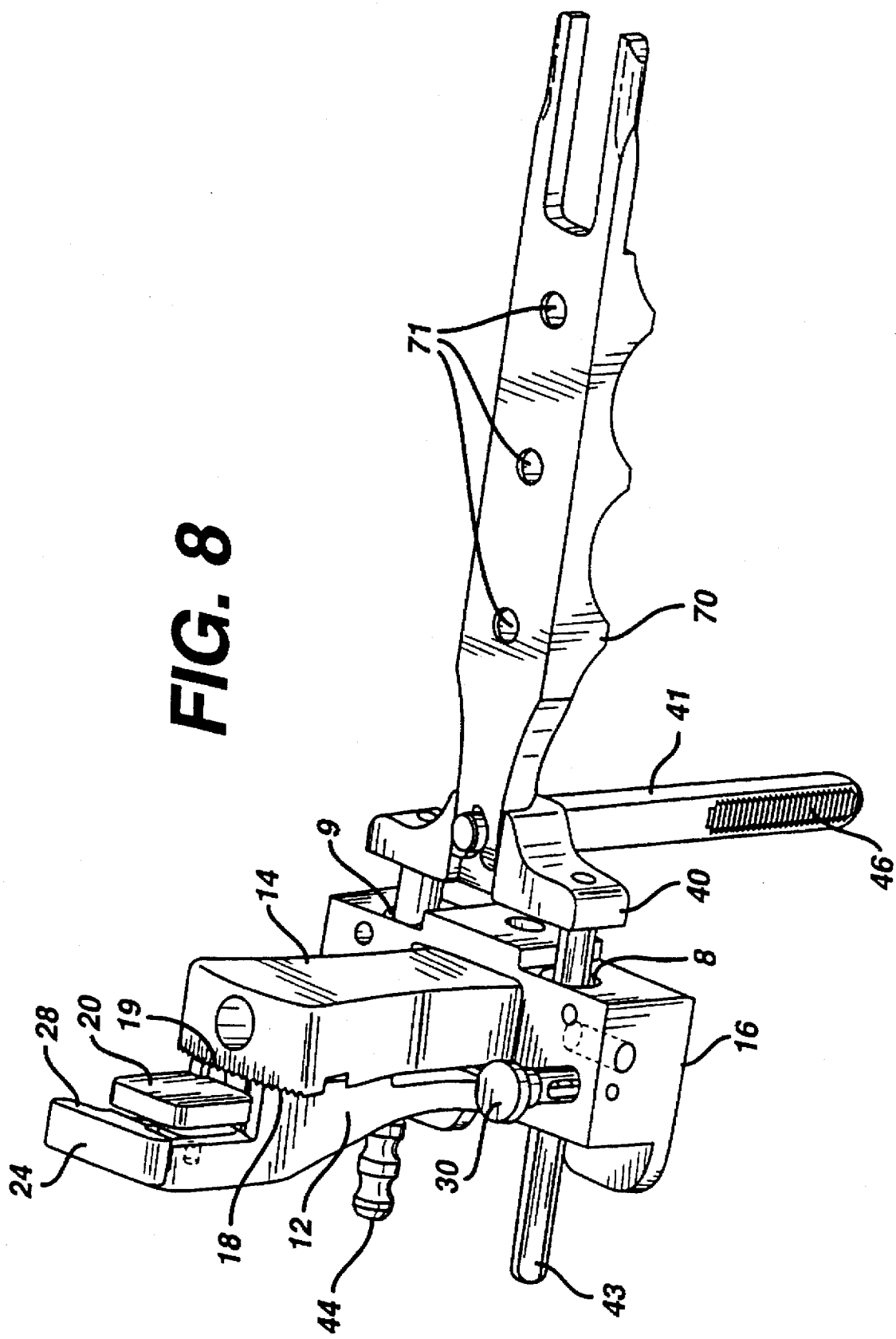
FIG. 8 illustrates a distal perspective view of the femoral locator with outrigger and alignment tower.
Figure 9:
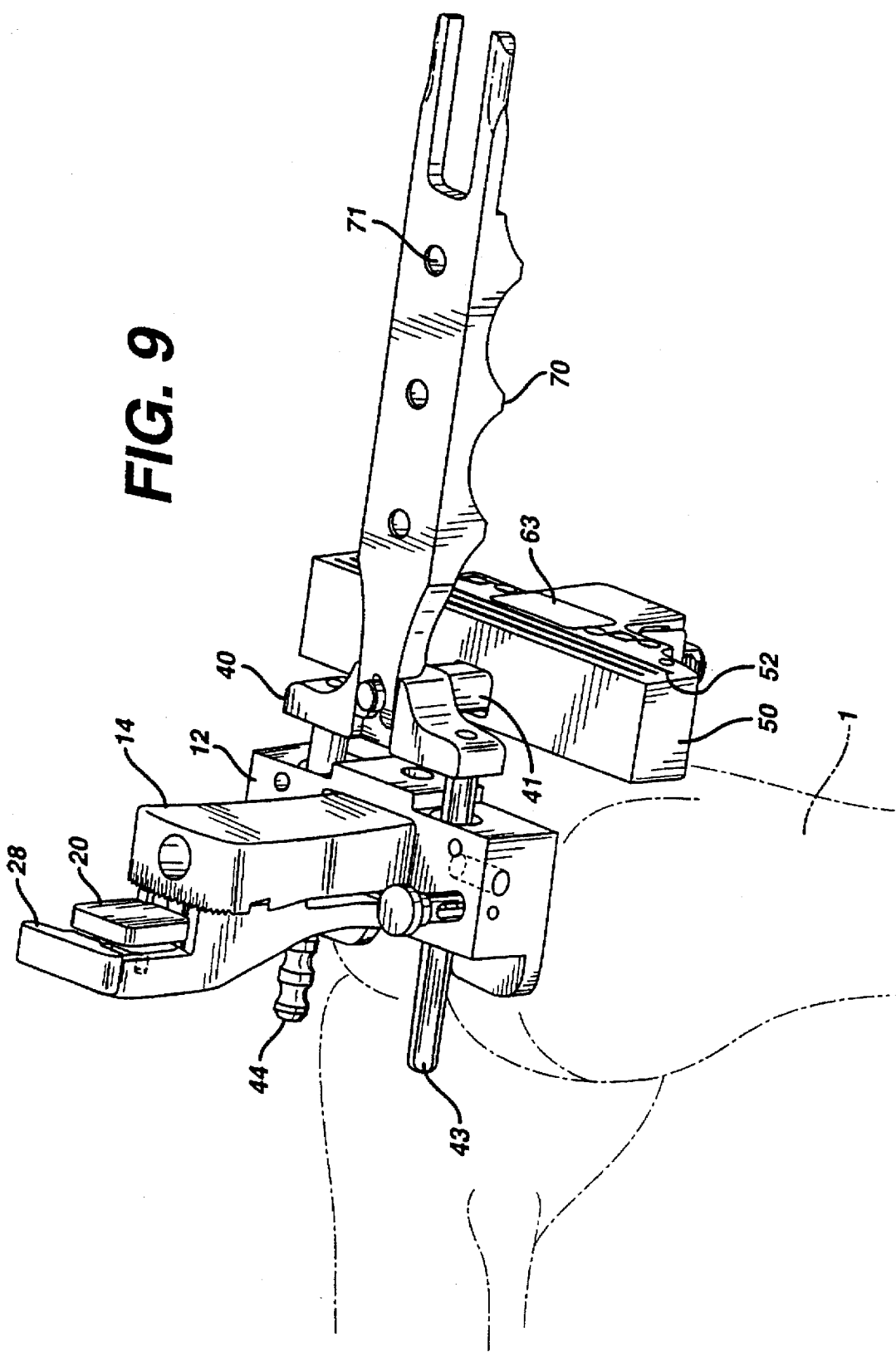
FIG. 9 illustrates the femoral locator, outrigger and alignment tower of FIG. 8 with the distal femoral cutting block attached.

The body 12 of the locator 10 has openings 8,9 for receiving legs 43, 44 of outrigger 40, respectively. When the outrigger is inserted into the body 12 as illustrated in FIG. 8, the shaft 41 extends proximally with respect to the femur.

The system of the preferred embodiment also comprises a cutting block 50 (FIGS. 10–12) comprising cutting slots 52 extending anterior-posterior, for receiving and guiding cutting elements (not shown) to make an initial cut in the femur distal end. The cutting block 50 also includes three sets of openings 55, 56, and 57 for receiving a pair of Steinmann pins (not shown) drilled into the femur 1 to secure the cutting block 50 in alignment with the femur 1. The openings 56 are similarly used while the other openings 55 and 57 are used to adjust the cut plane proximally or distally respectively. The cutting block 50 has a D-shaped opening 51 for receiving the shaft 41 of the outrigger 40 oriented so that the cutting slots 52 are in appropriate position extending anterior-posterior, for making the initial distal femoral cut.

In use, an intramedullary rod is inserted through opening 32 into the intramedullary canal of the femur to establish an anatomical axis. The femoral locator 10 is then placed on the intramedullary rod by way of opening 32. The femoral locator 10 is placed against the distal portion of the condyles. An outrigger 40 is attached to the body 12. An alignment tower 70 is attached to the outrigger 40 in a position parallel to the plane of the condyle interfacing end 16. The alignment tower 70 includes openings 71 for inserting external alignment rods (not shown).

An alignment rod is inserted into the openings 71. The locking member 24 is then placed in the unlocked position in which the button 20 is free to move, by pulling the locking ledge 28 away from the body 12. The button 20 is depressed to release the teeth 19 of the button 20 from the teeth 18 of the pivoting member 14. The pivoting member 14 is then free to pivot about the pin 15.

The body 12 is then rotated with respect to the pivoting member 14 to align the alignment rod with the mechanical axis. Methods of establishing a mechanical axis are generally known. When the appropriate angle is established, the button 20 is released engaging the pivoting member 14 with the body 12 in the desired angular orientation. The ledge 28 of the locking member 24 is then pushed in a position under the button 20, locking the body 12 and pivoting member 14 in the desired angular orientation with respect to each other. The effect is to orient the body 12 with respect to the mechanical axis so that the condyle interfacing end 16, perpendicular to the alignment rods, is then locked into a position perpendicular to the mechanical axis. When the desired angular orientation is locked into position, retractable pins 30 extending through condyle interfacing end 16 are driven into the distal condyles to hold the locator 10 in position.

Once the locator 10 has been used to align the initial cut angle and the locator 10 is secured to the distal condyles, the cutting block 50 may be attached to the locator 10 by way of the distal outrigger 40.

Another aspect of the invention provides a means to adjust the cut depth or thickness an incremental or other desired distance from the set distance or distances of the cutting block. In a preferred embodiment, the increments are 1 mm.

Accordingly, the distal cutting block 50 also includes a button 58 located proximally. The button 58 is rotatably coupled to the cutting block by way of pin 59. The button 58 includes a teeth 60 which when the button 58 is rotated in a first direction, extend into the D-shaped opening 51 of the cutting block 50 aligning with teeth 46 of outrigger 40. The button 58 when rotated in a second opposite direction removes the teeth 60 from the D-shaped opening 51. A spring 62 is set within the cutting block 50 adjacent the button 58 so that the button is biased towards the first direction in which the teeth 60 interrupt the D-shaped opening 51.

In use, the user squeezes the button 58 and then inserts D-shaped opening 51 of the cutting block 50 over the D-shaped shaft 41 of the outrigger 40. The shaft 41 of the outrigger 40 includes teeth 46 for engaging the teeth 60 when teeth 60 extend into the D-shaped opening 51. As the cutting block 50 is inserted over the shaft 41, the user may read distal resection numbers 47 on the outrigger 40 through a distal resection window 63 in the cutting block. The distal resection numbers indicate the distance of the primary slot 52a of the cutting block 50 to the distal condyle surface. When the desired distance is reached, the button 58 is released and the teeth 60 engage with teeth 46 of the outrigger 40.

Another aspect of the invention provides a means for raising and lowering the cutting block 50 with respect to the condyle portion to be cut. This is preferably done after the angle and cut depth have been adjusted.

Accordingly, the femoral locator body 12 includes a button 7 (FIG. 6) on the side of the body 12. The button 7 extends into an opening 5 in the side of the body 12. The opening 5 is perpendicular with respect to and partially interrupts opening 9 for receiving leg 44 of outrigger 40. Button 7 includes stem 4 extending into opening 5 and partially interrupting opening 9 for receiving leg 44. Stem 4 includes an indentation 3 which when adjacent opening 9 within opening 5, does not interrupt opening 9. The button 7 is biased in a direction away from body 12 by way of spring 6 located within opening 5 so that the distal portion 2 of the stem 4 interrupts the opening 9. The button 58 is held into place by pin 13 which also limits the movement of the stem 4 within the opening 5. When the button 7 is depressed, the indentation 3 of the stem 4 aligns adjacent the opening 9 thereby permitting the leg 44 of the outrigger 40 to move within the opening 9.

In use, the button 7 on the body 12 is depressed and the legs 43, 44 of the outrigger 40 are free to be inserted or to move within openings 8, 9 respectively. When the cutting block 50 is an appropriate distance from the condyle, the button 7 is released and the spring 6 moves the stem 4 of the button into a position where the distal portion 2 interferes with the opening 9, thus engaging a notch 45 in the leg 44 and preventing movement of the leg 44.

When the position is set, the Steinmann pins are drilled through holes 56 into the anterior cortex of the femur, securing the cutting block 50 to the femur. The outrigger 40 and femoral locator 10 may then be removed and the distal cut performed through one of the slots 52 in the cutting block 50.

This invention has been described in connection with specific embodiments involving a femoral locating device and system. Naturally, it will be understood by those skilled in the art that various changes and modifications may be made in the invention without departing from its scope, which is defined by the following claims and their equivalents.

What is claimed is:

1. A femoral locating system for aligning a distal femoral cut in a knee replacement procedure comprising:
   a femoral locating device comprising:
      a body having a condyle interfacing end;
      a pivoting alignment element coupled to said body to pivot about a pivot axis with respect to said body;
      a lumen extending through said pivoting alignment element and through said condyle interfacing end for receiving an intramedullary rod therethrough; and
      a locking portion coupled to said body, said locking portion releasably engageable with said pivoting alignment element in a plurality of angular orientations with respect to the pivot axis to lock said pivoting alignment element in one of said plurality of angular orientations.

2. The femoral locating system of claim 1 further comprising an outrigger to be coupled to said femoral locating device, said outrigger for receiving a distal femoral cutting block to align said cutting block with respect to said body of said locating device, wherein said outrigger comprises:
   an attachment portion for coupling said outrigger to said body in a plurality of perpendicularly aligned positions with respect to said body; and
   wherein said body further comprises a selection device selectably engageable with said attachment portion for selecting and locking said outrigger to said body in one of said plurality of perpendicularly aligned positions.

3. The femoral locating system of claim 2 further comprising:
   a distal femoral cutting block arranged to couple with said outrigger;
   said outrigger further comprising a cutting block attachment portion for receiving said cutting block in a plurality of distal-proximal positions, said cutting block comprising a selection device for selecting and locking said cutting block to said outrigger in one of said plurality of distal-proximal positions.

4. The femoral locating system of claim 1 wherein said locking portion comprises a release mechanism for releasing said locking portion from engagement with said pivoting alignment element.

5. The femoral locating system of claim 1 wherein said pivoting alignment element further comprises a plurality of incremental engaging elements to engage said pivoting alignment element in plurality of predetermined angular orientations.

6. The femoral locating system of claim 1 wherein said pivot axis is parallel with said condyle interfacing end.

7. The femoral locating system of claim 2 wherein said condyle interfacing end comprises a condyle interfacing surface defining a plane; p1 said femoral locating system further comprising an intramedullary rod insertable through said lumen and into the intramedullary canal of a distal femur; and an alignment tower coupled to said outrigger in a position parallel to a plane of said condyle interfacing end, said alignment tower comprising at least one opening for receiving an external alignment rod.

8. The femoral locating system of claim 7 wherein said pivot axis is parallel with said condyle interfacing surface.

9. The femoral locating system of claim 2 wherein said selection device of said body comprises a means for engaging said outrigger in a plurality of discrete anterior-posterior positions.

10. A method of aligning a femoral distal cut in preparing a distal femur for a prosthetic knee implant comprising:

inserting an intramedullary rod in the intramedullary canal of a distal femur;

providing a femoral locating device comprising:
    a body having a condyle interfacing surface;
    a pivoting alignment element coupled to said body to pivot about a pivot axis parallel to said condyle interfacing surface; and
    a lumen extending through said pivoting alignment element and through said condyle interfacing surface;

providing an outrigger comprising an attachment portion for coupling said outrigger to said body in at least on perpendicularly aligned position with respect to said body;

inserting said femoral locating device on said intramedullary rod with said interfacing surface abutting the distal end of the femur;

coupling the outrigger to the body in a perpendicularly aligned position with respect to the body;

providing an alignment tower comprising at least one opening for receiving an external alignment rod;

coupling said alignment tower to said outrigger in a position parallel to a plane of said condyle interfacing surface;

inserting an external alignment rod into said opening perpendicular to said condyle interfacing surface;

pivoting the body with respect to the pivoting alignment element until the external alignment rod is aligned with the mechanical axis of the femur;

inserting a cutting block on said outrigger; and making a distal femoral cut in alignment with the mechanical axis defined by the location of the condyle interfacing surface.

\* \* \* \* \*

UNITED STATES PATENT AND TRADEMARK OFFICE
CERTIFICATE OF CORRECTION

PATENT NO. : 5,676,668
DATED : October 14, 1997
INVENTOR(S) : Diana McCue, et. al.

It is certified that error appears in the above-identified patent and that said Letters Patent is hereby corrected as shown below:

Column 7, line 1, after "plane" delete --P1--; and "said" should start a a new paragraph--.

Signed and Sealed this

Tenth Day of February, 1998

Attest:

BRUCE LEHMAN

*Attesting Officer*     *Commissioner of Patents and Trademarks*